United States Patent [19]

Blaha

[11] Patent Number: 4,461,551
[45] Date of Patent: Jul. 24, 1984

[54] PORTABLE OPHTHALMOLOGICAL INSTRUMENT FOR SELECTIVE EXAMINATION OF ANTERIOR OR POSTERIOR REGIONS OF THE EYE

[75] Inventor: Erich Blaha, Essingen, Fed. Rep. of Germany

[73] Assignee: Carl-Zeiss-Stiftung, Oberkochen, Fed. Rep. of Germany

[21] Appl. No.: 375,296

[22] Filed: May 5, 1982

[30] Foreign Application Priority Data

May 27, 1981 [DE] Fed. Rep. of Germany ... 8115734[U]

[51] Int. Cl.³ ............................................... A61B 3/10
[52] U.S. Cl. .................................. 351/214; 351/221; 351/216
[58] Field of Search ............... 351/213, 214, 221, 216, 351/217, 218

[56] References Cited

U.S. PATENT DOCUMENTS 3,830,562 8/1974 McGrann ............................ 351/214

Primary Examiner—John K. Corbin
Assistant Examiner—Rodney B. Bovernick
Attorney, Agent, or Firm—Hopgood, Calimafde, Kalil, Blaustein & Judlowe

[57] ABSTRACT

The invention contemplates structure for such combinable use of a portable ophthalmoscopy light and a portable stereomicroscope that components are readily convertible to selectively provide ophthalmoscope functions for examination of posterior regions of an eye, and slit-lamp functions for examination of anterior regions of the eye. Knob adjustment of the housing of the ophthalmoscopy light provides selective availability of circular and slit diaphragms, as well as filters, as appropriate to the particular kind of observation to be made.

5 Claims, 5 Drawing Figures

PORTABLE OPHTHALMOLOGICAL INSTRUMENT FOR SELECTIVE EXAMINATION OF ANTERIOR OR POSTERIOR REGIONS OF THE EYE

BACKGROUND OF THE INVENTION

The present invention relates to a portable ophthalmological instrument for selective examination of anterior or posterior regions of the eye.

It is known that a portable ophthalmoscopy light source instrument can be used to examine the fundus of an eye with an inverted image, that is, when examining the posterior region of the eye. Such an instrument consists of a tubular housing which contains a source of light, a condenser, an iris diaphragm, a knob for the optional introduction of a color filter, an objective, as well as a deflection prism at the light-exit end. In making his examination, the doctor holds this ophthalmoscopy light source instrument in one hand while holding in his other hand an ophthalmoscopic magnifier in front of the patient's eye.

To facilitate observation, a so-called stereoviewer can be placed over the known ophthalmoscopy light source instrument. The doctor can then, after attaching this additional part, stereoscopically observe the posterior region of the eye.

Observation of the anterior regions of the eye is not possible with this known ophthalmoscopy light source instrument. These regions of the eye are customarily examined by means of a slit lamp which is mounted stationary.

A hand-held slit lamp with binocular microscope is also known. In this known portable instrument, a slit-lamp illumination is arranged to the side of the binocular microscope at a fixed angle to the optical axis of the latter. It produces in the anterior region of the eye to be observed a slit image which is stereoscopically observed through the binocular microscope. The instrument is provided with a cheek support which is applied to the lower boney edge of the eye socket of the patient. For focusing, this resting surface can be axially adjusted with respect to the instrument. When making an examination of the patient, the entire instrument is moved in order to scan the surface of the eye, the cheek support being used as a fulcrum.

This known portable slit lamp is suitable only for examination of the anterior regions of the eye.

BRIEF STATEMENT OF THE INVENTION

The object of the present invention is to provide a low-cost portable ophthalmological instrument for selective examination of anterior and posterior regions of the eye, the instrument involving only a few manipulations for conversion from one to the other of the different examinations.

The invention achieves this object by employing an ophthalmoscopy light source instrument having a tubular housing and a deflection prism at its light-exit end. A stereomicroscope is associated with this light, via an arcuate guide that is firmly connected to the stereomicroscope, and a sleeve which is displaceable along the guide is also adapted for connection to the tubular housing of the lignt source instrument. The sleeve carries a supplementary lens which, upon light-housing assembly to the sleeve, is located in front of the deflection prism of the ophthalmoscopy light. And the light source housing mounts a control knob for the optional introduction of a circular diaphragm and of at least one slit diaphragm into the illumination-ray path.

In one employment of this apparatus, the ophthalmoscopy light source in the tubular housing may be used by itself, in which case the circular diaphragm is swung into the illuminating-ray path, and indirect ophthalmoscopy, i.e., observation of the posterior regions of the eye, may be carried out with the aid of an ophthalmoscopic magnifier.

For examination of anterior regions of the eye, the arcuately guided sleeve of the stereomicroscope is placed over the housing of the ophthalmoscopy light source, thus automatically positioning a supplementary lens in front of the deflection prism of the ophthalmoscopy light source housing. Also, the control knob is actuated to swing a slit diaphragm into the illumination-ray path of the ophthalmoscopy light source instrument. This diaphragm is now imaged via the supplementary lens in the anterior region of the eye.

For his examination, the doctor holds the entire combined instrument in his hands and places the resting surface of the spacer against the forehead of the patient. Through readily changed spacer length, focusing is effected at the region of the eye to be examined, and the spacer length thus determined is secured.

In the indicated use, the ophthalmoscopy light source instrument acts as a slit-lamp illuminator. The slit image it produces can be swung within a given angular range about the eye of the patient by displacing the light source housing along the arcuate guide of the stereomicroscope.

To avoid unintentional displacement of the slit image in the event of an oblique position of the entire instrument, as is readily possible when the patient is lying down for his examination, the arcuate guide is provided with a plurality of detent positions for the sleeve.

DETAILED DESCRIPTION

The invention will be described in detail in conjunction with the accompanying drawings, in which.

Figure 1:
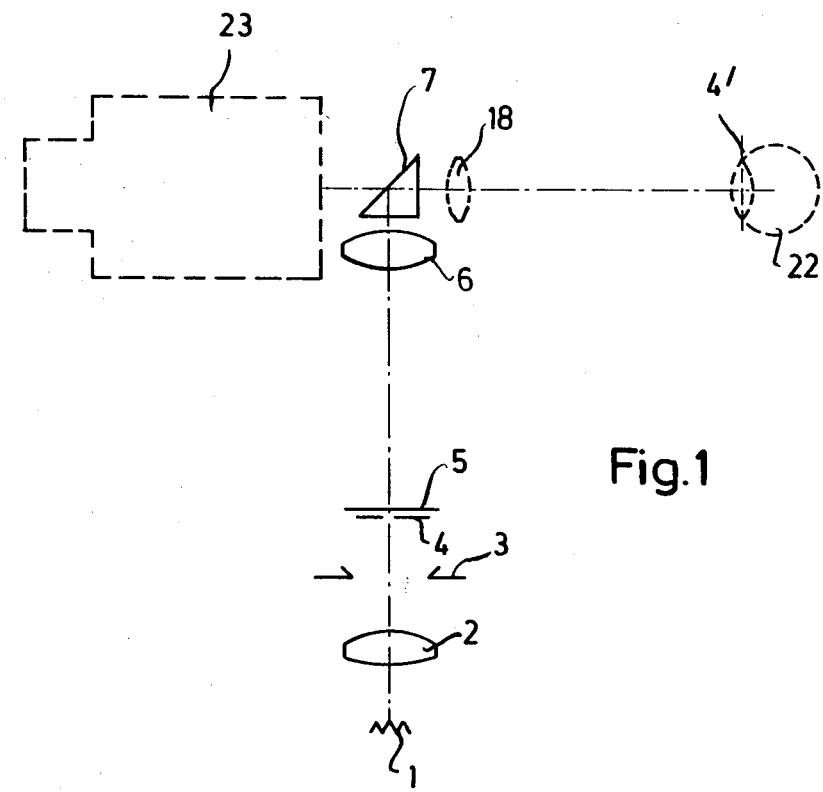
FIG. 1 is a diagrammatic view of optical elements of the instrument of the invention.

In FIG. 1, solid lines indicate components of an ophthalmoscopy light source instrument, wherein 1 is a source of light and 2 is a condenser. Within the illumination-ray path there is arranged an adjustable iris diaphragm 3, as well as a diaphragm 4 and a filter 5, each of which can be selectively swung into the ray path. Light passing through these elements is so imaged by a stationary objective 6 and a deflection prism 7 into the eye to be examined that the retina of the eye is uniformly illuminated. By means of a preferably aspherically developed ophthalmoscopic magnifier, the doctor then examines the eye of the patient in accordance with the known principle of indirect ophthalmoscopy. In this situation, diaphragm 4 is developed as a circular diaphragm which does not mask rays passing through the iris diaphragm 3.

Figure 2:
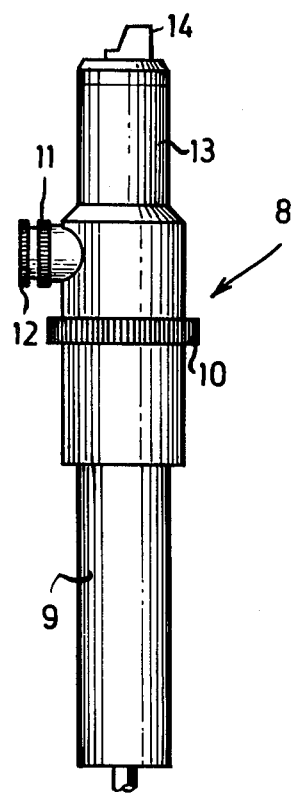
FIG. 2 is a side view of an ophthalmoscopy light source instrument.

FIG. 2 shows the tubular housing 8 for the elements described in connection with FIG. 1. A power supply or battery for supplying current to lamp 1 may be contained within the lower part 9 of the housing. This part of the housing is hand-held by the doctor. An adjustment ring 10 is for setting the iris diaphragm 3. A knob or ring 12 serves for swinging a selected one of at least two diaphragms into the ray path, one of these diaphragms being developed as a circular diaphragm and the other as a slit diaphragm. A further adjustment ring 11 serves for swinging a preselected color filter, for instance a green filter or a blue filter, into the ray path. The selectively available color filters at 5 and diaphragms at 4 are advantageously disposed in coaxial Rekoss sleeves, not shown.

The upper housing part 13 is of cylindrical development and carries the deflection prism 7 within a mount 14.

Figure 3:
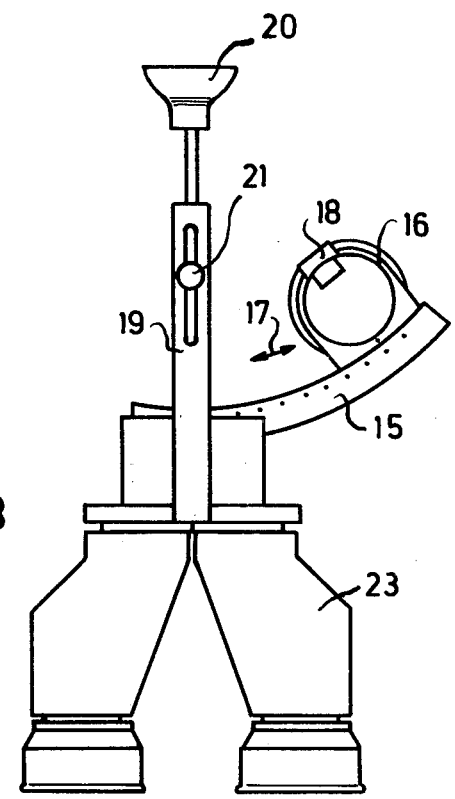
FIG. 3 is a plan view of a stereomicroscope developed in accordance with one embodiment of the invention.

In FIG. 3, a stereomicroscope 23 comprises two ocular tubes, adjustable to the interpupillary distance of the observer, and a microscope objective. Rigidly attached to the housing of stereomicroscope 23 is an arcuate guide 15 which can be positioned and secured optionally for left-hand or right-hand use. A sleeve 16 is mounted therein for guided displacement, as suggested by the double arrow 17. The sleeve 16 carries a supplementary lens 18.

In addition, a spacer 19 is firmly attached to the stereomicroscope 23, and spacer 19 includes a spring-loaded extension by which spacer length is adjustable. The spring loading is outward, and a clamping screw 21 serves to fix a desired spacer length. A resting foot or pad 20 of soft material is provided at the front end of spacer 19.

If the ophthalmological instrument of the invention is to be used as a hand-held slit lamp, then sleeve 16 (attached to the stereomicroscope 23) is pushed over the upper part 13 of the tubular housing 8 and is firmly connected thereto, as by means of a bayonet lock. The resulting portable slit lamp is shown in FIG. 4, while its optical construction is shown in dotted lines in FIG. 1.

Figure 5:
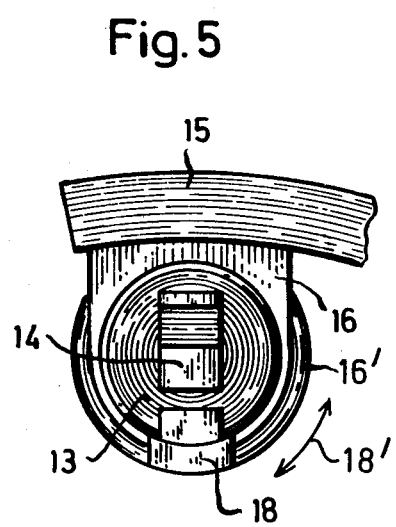
FIG. 5 is an enlarged fragmentary plan view of the ophthalmoscopy light in the combination shown in FIG. 4.

When the sleeve 16 is thus assembled to housing part 13, the supplementary lens 18 which is carried by sleeve 16 is, as shown in FIG. 5, automatically positioned in front of the housing or mount 14 for the deflection prism 7.

Figure 4:
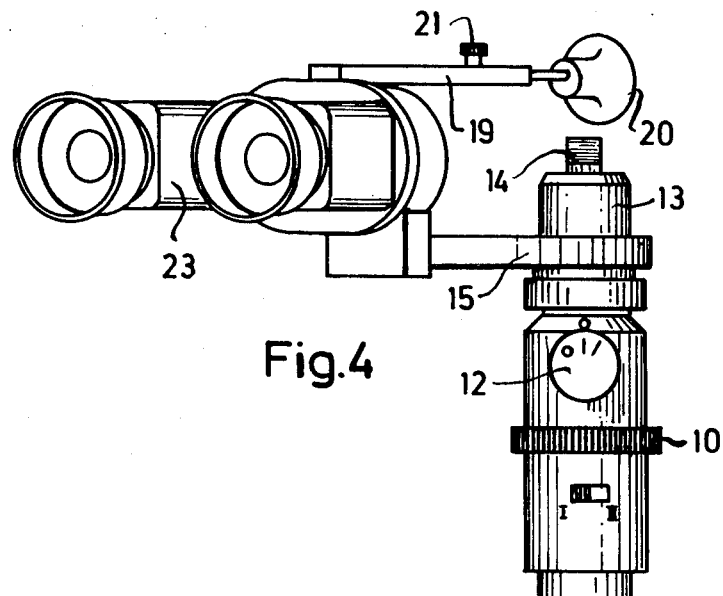
FIG. 4 is a view in side elevation to show the instruments of FIGS. 2 and 3 combined, the ophthalmoscopy light of FIG. 2 being as viewed in the direction toward the left side of the view of FIG. 2.

Now, if a slit diaphragm is brought into illumination-ray path, by indicium selection at 12 as suggested in FIG. 4, an image 4' of the slit diaphragm 4 may be obtained in the anterior region of the eye 22 of the patient to be examined. This image is observed via the stereomicroscope 23. To make the examination, the resting foot 20 is placed against the patient's forehead, and focusing is effected on the eye region to be observed, by changing the length of spacer 19.

The arcuate guide 15 has a plurality of detent positions for sleeve 16 in order to avoid unintentional displacement thereof; these positions are suggested by spaced dots in FIG. 3.

The instrument of the invention can also be developed as a binocular ophthalmoscope. For this purpose, the supplementary lens 18 is swingably mounted to sleeve 16, so that it can be swung out of the ray path; such swingable mounting is suggested by a double arrow 18' in FIG. 5, wherein lens 18 is seen to be carried by an adjustable ring 16' concentric with the axis of the supported housing part 13, ring 16' being rotatably carried by sleeve 16. For ophthalmoscopic examination with the combined instrument of FIG. 4, a circular diaphragm is selected by manipulation at 12, lens 18 is swung out of the ray path, and the ophthalmoscopy light source within housing 8 is swung in the arcuate guide 15 until the deflection prism 14 is positioned between the viewing openings of the stereomicroscope 23.

What is claimed is:

1. A portable ophthalmological instrument for selective examination of anterior or posterior regions of the eye, comprising an ophthalmoscopy light source in a tubular housing and having a deflection prism at its light-exit side, characterized by the fact that a stereomicroscope (23) is firmly connected with an arcuate guide (15) within which a sleeve (16) is displaceably supported, that said sleeve (16) is adapted for detachable assembly to part of the tubular housing (13) and that said sleeve carries a supplementary lens (18) which, upon such assembly, is positionable in front of the deflection prism (7) of the ophthalmoscopy light source (8), and that said light housing (8) is further provided with a selector means (12) for optionally bringing a circular diaphragm and at least one slit diaphragm (4) into the illumination-ray path.

2. A portable ophthalmological instrument according to claim 1, characterized by the fact that the arcuate guide (15) has a plurality of detent positions for the sleeve (16).

3. A portable ophthalmological instrument according to claim 1 or claim 2, characterized by the fact that a spacer (19) is connected with the stereomicroscope (23) and includes a spring-loaded extension for forehead contact and resilient adjustment of spacer length, and a forehead resting foot (20) at the outer end of the extension.

4. A portable ophthalmological instrument according to claim 3, characterized by the fact that the spacer (19) includes clamp means (21) to fix an adjusted spacer length.

5. A portable ophthalmological instrument according to claim 1, characterized by the fact that the supplementary lens (18) is arranged swingably mounted to said sleeve in such manner that it can be swung out of the ray path.

* * * * *